US00PP37733P2

(12) United States Plant Patent
Wyckstandt

(10) Patent No.: US PP37,733 P2
(45) Date of Patent: Oct. 6, 2026

(54) *AGAPANTHUS* PLANT NAMED 'Vitro 002'

(50) Latin Name: ***Agapanthu* hybrid**
Varietal Denomination: Vitro 002

(71) Applicant: Tim Wyckstandt, Aalter (BE)

(72) Inventor: Tim Wyckstandt, Aalter (BE)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/422,451

(22) Filed: Dec. 17, 2025

(30) Foreign Application Priority Data

Jul. 29, 2025 (QZ) ..... PBR 20251689

(51) Int. Cl.
*A01H 6/04* (2018.01)
*A01H 5/02* (2018.01)

(52) U.S. Cl.
USPC ..... Plt./398

(58) Field of Classification Search
USPC ..... Plt./398
CPC ..... A01H 6/04; A01H 5/02
See application file for complete search history.

*Primary Examiner* — Keith O. Robinson
(74) *Attorney, Agent, or Firm* — Penny J. Aguirre

(57) ABSTRACT

A new cultivar of *Agapanthus* plant named 'Vitro 002' that is characterized by its floriferous and long flowering period with good re-blooming until frost, its white flowers with yellow filaments, and its tall plant height (average of 80 cm), yet compact plant habit.

3 Drawing Sheets

Botanical classification: *Agapanthus* hybrid.
Varietal denomination: 'Vitro 002'.

CROSS REFERENCE TO RELATED APPLICATIONS

This application claims priority to European Community Plant Variety Office (CPVO) Plant Breeder's Rights Application No. 2025/1689, filed Jul. 29, 2025. This application is co-pending with U.S. Plant Patent Applications filed for plant patents derived from the same breeding program that is entitled *Agapanthus* Plant Named 'A19002' (U.S. Plant patent application Ser. No. 19/422,442), *Agapanthus* Plant Named 'A21001' (U.S. Plant patent application Ser. No. 19/422,443), *Agapanthus* Plant Named 'A22004' (U.S. Plant patent application Ser. No. 19/422,445), and *Agapanthus* Plant Named 'Su Casa' (U.S. Plant patent application Ser. No. 19/422,434).

BACKGROUND OF THE INVENTION

The present invention relates to a new and distinct cultivar of *Agapanthus* of hybrid origin and will be referred to hereafter by its cultivar name, 'Vitro 002'. 'Vitro 002' represents a new perennial grown for landscape and container use.

The new cultivar was derived from a controlled breeding program by the Inventor in Aalter, Belgium. The goal of the breeding program was to develop a new cultivar of *Agapanthus* with a tall plant height and self-cleaning white flowers that bloom for a long period of time until frost. The new cultivar arose from open-pollination of *Agapanthus* 'Marijke' (not patented) in August of 2020. The male parent is therefore unknown. 'Vitro 002' was selected as a single unique plant after evaluation of 10,000 resulting seedlings in July of 2021.

Asexual propagation of the new cultivar was first accomplished by division by the Inventor in Aalter, Belgium in August of 2021. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'Vitro 002' as a distinct cultivar of *Agapanthus*.

1. 'Vitro 002' exhibits a floriferous and long flowering period with good re-blooming until frost.
2. 'Vitro 002' exhibits white flowers with yellow filaments.
3. 'Vitro 002' exhibits a tall plant height (average of 80 cm), yet compact plant habit.

The female parent of 'Vitro 002' differs from 'Vitro 002' in having a shorter flowering period and violet-blue flowers. 'Vitro 002' can be most closely compared to the *Agapanthus* cultivars 'AAOPR017' (not patented) and 'Verag W01' (not patented). 'AAOPR017' is similar to 'Vitro 002' in having white flowers. 'AAOPR017' differs from 'Vitro 002' in having more grey-green foliage, a shorter plant height, a shorter flowering period, and in being less floriferous. 'Verag W01' is similar to 'Vitro 002' in having white flowers and a long flowering period. 'Verag W01' differs from 'Vitro 002' in having a much shorter plant height, shorter leaves, and smaller inflorescences.

'Vitro 002' can also be compared to the co-pending cultivars of *Agapanthus*; 'A19002', 'A21001', 'A22004' and 'Su Casa'. 'A19002' differs from 'Vitro 002' in having white flowers. 'A21001' differs from 'Vitro 002' in having deep blue flowers with blue filaments. 'A22004' differs from 'Vitro 002' in having violet-blue flowers with a darker central stripe on the tepals. 'Su Casa' differs from 'Vitro 002' in light violet-blue flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the effective filing date.

BRIEF DESCRIPTION OF THE DRAWINGS

The accompanying color photographs illustrate the overall appearance and distinct characteristics of the new *Agapanthus*. The photographs were taken of a plant 19 months in age of 'Vitro 002' as grown in an unheated poly-covered tunnel in a 19-cm container in Aalter, Belgium.

The photograph in FIG. 1 provides a side view of a plant of 'Vitro 002' in bloom.

Figure 1:
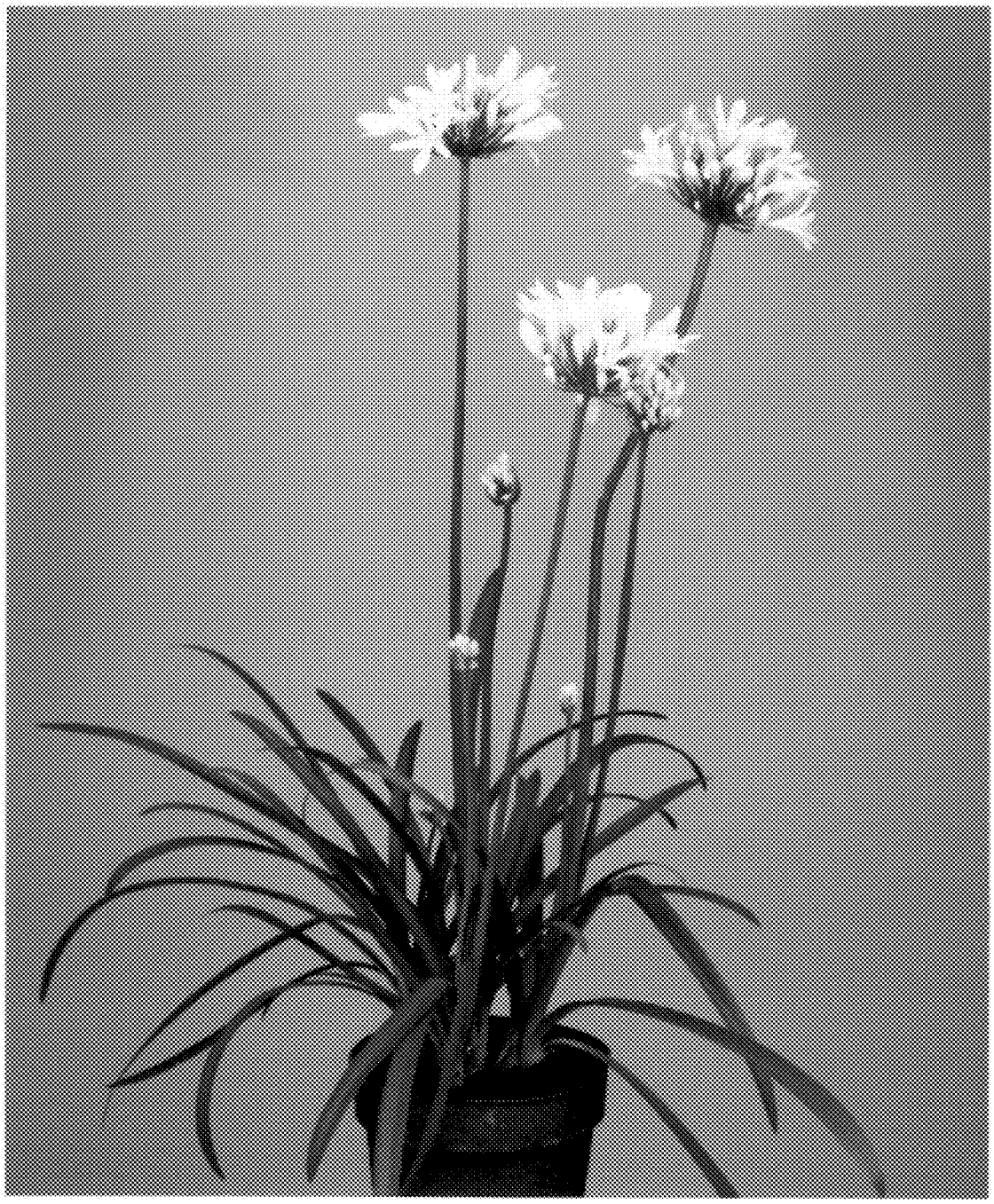
Figure 2:
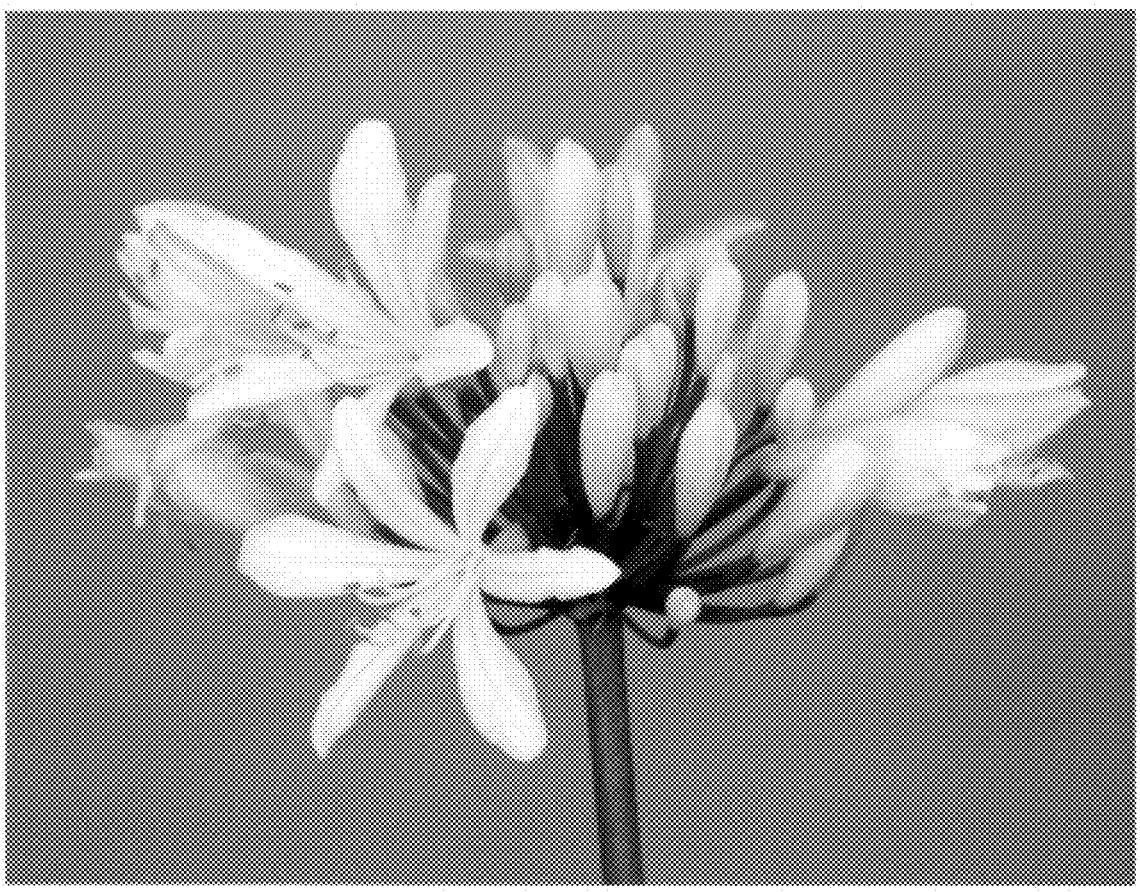

The photograph in FIG. 2 provides a close-up view of an inflorescence of 'Vitro 002'.

Figure 3:
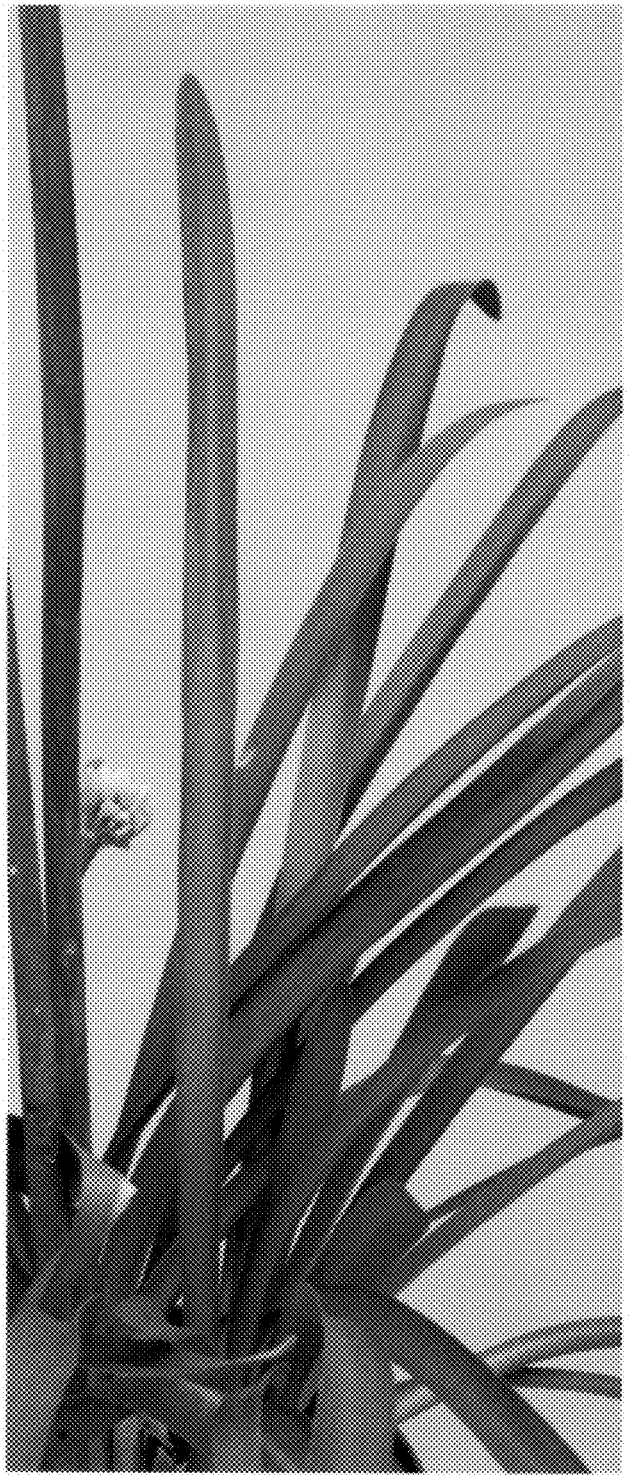

The photograph in FIG. 3 provides a close-up view of the foliage of 'Vitro 002'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 19-month-old plants of 'Vitro 002' as grown in an unheated poly-covered tunnel in 19-cm containers in Aalter, Belgium. The phenotype of the new cultivar may vary with variations in environmental, climatic, and cultural conditions, as it has not been tested under all possible environmental conditions. The color determinations are in accordance with The 2015 (2019 reprint) Colour Chart of The Royal Horticultural Society, London, England, except where general color terms of ordinary dictionary significance are used.

General description:

*Blooming period*.—End of May until November (frost) in Belgium.

*Plant type*.—Semi-deciduous (climate dependent) herbaceous perennial.

Plant habit.—Basal rosettes with inflorescences emerging from the rosette center.

*Height and spread*.—An average of 80 cm in height and 80 cm in spread as grown in the landscape.

*Hardiness*.—At least in U.S.D.A. Zones 8 to 12.

*Diseases and pests*.—No resistance or susceptibility to diseases or pests has been observed.

*Root description*.—Thick and fleshy.

*Propagation*.—Division and Tissue culture.

Foliage description:

*Leaf shape*.—Ligulate.

*Leaf division*.—Simple.

*Leaf base*.—Decurrent, cuneate to broadly cuneate.

*Leaf apex*.—Acute.

*Leaf aspect*.—Moderately carinate, slightly to moderately curved.

*Leaf venation*.—Parallel, upper surface; a blend of 137B and 146A, lower surface; 144B.

*Leaf margins*.—Entire.

*Leaf size*.—Up to 35.1 cm in length and up to 1.8 cm in width.

*Leaf surface*.—Both surfaces non-rugose, upper surface slightly glossy, lower surface very slightly glossy.

*Leaf number*.—Average of 7 leaves per rosette.

*Foliage density*.—Medium.

*Leaf color*.—Young leaves upper surface; 146A, young leaves lower surface; 146B, mature leaves upper surface; a blend of 137B and 146A, mature lower surface; 144B.

*Leaf attachment*.—Sessile to base.

Flower description:

*Inflorescence type*.—Umbel, hemispherical.

*Flower fragrance*.—None.

*Flower type*.—Rotate, campanulate, base of tepals fused.

*Flower number*.—An average of 40 flowers per umbel, 400 buds and flowers per plant.

*Inflorescence size*.—Average of 8.7 cm in height and 14.1 cm in diameter.

*Flower size*.—An average of 4 cm in depth, 4.8 cm in diameter, throat 4 mm in diameter, tube 1.2 cm in length and 3 mm in diameter.

*Lastingness of inflorescence*.—10 days, self-cleaning.

*Flower aspect*.—Primarily upright to pedicel.

*Peduncle*.—1 per rosette, very sturdy, oval in shape, held primarily upright 80° to soil level, surface is glabrous, slightly glaucous and moderately glossy, average of 56.7 cm in length and 8 mm in diameter, color; 144A with thin waxy glaucous layer 193D.

*Pedicels*.—Oval in shape, held in multiple angles, surface is glabrous and glossy, average of 2.9 cm in length and 1.7 mm in diameter, 143A in color.

*Flower buds*.—Oblanceolate in shape, matte surface and slightly velvety, average of 2.8 cm in length and 9 mm in width, color; NN155B, base 157B, axially apex 160B.

*Tepals* (*perianth*).—6, 2 whorls (3 upper and 3 lower), rotate, oblanceolate in shape, fused base, entire margins, apex; lower tepals acute, upper tepals bluntly acute, surface all tepals; glabrous, slightly velvety, non-rugose, thick substance, all tepals 4.3 cm in length, lower tepal 7 mm in width, upper tepal 1.1 cm in width, color (all tepals); when opening upper and lower surface; NN155D, when fully open upper surface NN155D, when fully open lower surface NN155D, base NN155C.

*Bracts*.—Immature inflorescence covered with 1 bract; dropped when individual flowers develop to open, broadly ovate in shape, 2.8 cm in length, 2 cm in width, color; upper surface a blend of 165C and 165D, lower surface 167C with apex 165D, veins on both surfaces 165B, pedicel bract; a single bract is present at base, filiform in shape, 2 cm in length, 0.5 mm in width, color; 158D with apex 161C.

Reproductive organs:

*Gynoecium*.—Pistil; 1, average of 2.4 cm in length, stigma; club-shaped, NN155A in color, style; 2.3 cm in length, NN155A in color, ovary; oblong in shape, 1 cm in length, 4 mm in width and 154D in color, pistillodes not present.

*Androecium*.—Stamens; 6, anthers; basifixed, oblong in shape, 2.5 mm in length, 1 mm in width, 163B in color, filament; 2.1 cm in length, NN155D in color, pollen; moderate in quantity and 14B in color, staminodes not present.

*Fruit/seed*.—None observed to date.

It is claimed:

1. A new and distinct cultivar of *Agapanthus* plant named 'Vitro 002' as herein illustrated and described.

* * * * *